(12) United States Patent
Leung et al.

(10) Patent No.: US 8,940,029 B2
(45) Date of Patent: Jan. 27, 2015

(54) VARIABLE LOCKING BONE PLATING SYSTEM

(71) Applicant: Biomet Trauma, LLC, Warsaw, IN (US)

(72) Inventors: Ross T. Leung, Piscataway, NJ (US); Brian K. Berelsman, Warsaw, IN (US)

(73) Assignee: Biomet Trauma, LLC, Warsaw, IN (US)

( * ) Notice: Subject to any disclaimer, the term of this patent is extended or adjusted under 35 U.S.C. 154(b) by 199 days.

(21) Appl. No.: 13/650,165

(22) Filed: Oct. 12, 2012

(65) Prior Publication Data

US 2013/0096631 A1    Apr. 18, 2013

Related U.S. Application Data

(60) Provisional application No. 61/547,772, filed on Oct. 17, 2011.

(51) Int. Cl.
*A61B 17/80* (2006.01)
*A61B 17/86* (2006.01)

(52) U.S. Cl.
CPC .......... *A61B 17/8057* (2013.01); *A61B 17/8605* (2013.01)
USPC .......................................... 606/291; 606/287

(58) Field of Classification Search
USPC .................. 606/280–281, 286–287, 289, 291
See application file for complete search history.

(56) References Cited

FOREIGN PATENT DOCUMENTS

EP            2248479 A1    11/2010
WO    WO-2011076205 A1     6/2011

OTHER PUBLICATIONS

Written Opinion of the International Searching Authority regarding International Application No. PCT/US2012/059993, mailed Mar. 1, 2013.

*Primary Examiner* — Nicholas Woodall
*Assistant Examiner* — Larry E Waggle, Jr.
(74) *Attorney, Agent, or Firm* — Harness, Dickey

(57) ABSTRACT

An apparatus can include a plate member having a top surface, a bottom surface and a hole extending between the top and bottom surfaces. The plate member hole can have a spherically shaped sidewall. A right-hand helical thread can be formed in the sidewall of the plate member hole, and a left-hand helical cut can be formed in the sidewall of the plate member hole intersecting the right-hand helical thread. The left-hand helical cut can be configured to reduce a portion of a contact surface area of the right-hand helical thread and the sidewall of the plate member hole.

54 Claims, 13 Drawing Sheets

VARIABLE LOCKING BONE PLATING SYSTEM

CROSS-REFERENCE TO RELATED APPLICATIONS

This application claims the benefit of U.S. Provisional Application No. 61/547,772, filed on Oct. 17, 2011. The entire disclosure of the above application is incorporated herein by reference.

FIELD

The present disclosure relates generally to a bone plating system and, more particularly, to a variable locking bone plating system.

BACKGROUND

This section provides background information related to the present disclosure that is not necessarily prior art.

In certain orthopedic procedures, it can be necessary to secure multiple bones or bone portions relative to each other to facilitate proper healing. For example, it is frequently necessary to secure two or more portions of a broken long bone to ensure proper healing. This need may be the result of physical trauma from fractures or dislocations, degenerative diseases, or tumors.

Common methods of fracture treatment include casting and external fixation. It is also known to treat fractures with internal plating systems. Use of such plating systems involves the attachment of a plate to the bone with bone screws. The plating systems function to stabilize discrete bone portions and thereby facilitate fusion of the bone portions in a particular orientation for healing or to repair a condition of the patient.

Plating systems that use locking screws are generally known. One known plating system is shown in German Patent Application No. DE 43 43 117. This German application illustrates a bone plate with threaded holes for locking screws with externally threaded heads. The locking screw is inserted coaxially with the threaded hole in the bone plate.

It may also be desirable for a surgeon to be able to insert a locking bone screw through a bone plate hole at a selected angle to the bone plate. Various bone plate systems having such "polyaxial" capability are also generally known. These known systems, however, typically employ a bushing or expandable ring that is movable within the bone plate hole. As the bone screw is threaded into the bone through the bushing or ring, the head of the bone screw expands the bushing or ring against the bone plate hole wall thereby friction locking the bone screw at the desired angle. Such polyaxial bone plate systems, however, can be difficult to manipulate during surgery, as well as require an additional component (i.e., bushing or ring) to facilitate the polyaxial capability which increases the complexity of the system.

Thus, while polyaxial bone plate systems have generally worked for their intended purpose, there remains a need for continuous improvement in the relevant art.

SUMMARY

This section provides a general summary of the disclosure, and is not a comprehensive disclosure of its full scope or all of its features.

In one form, an apparatus is provided in accordance with various aspects of the present teachings. The apparatus can include a plate member having a top surface, a bottom surface and a hole extending between the top and bottom surfaces. The hole can have a spherically shaped sidewall. A right-hand helical thread can be formed in the sidewall of the hole, and a left-hand helical cut can be formed in the sidewall of the hole intersecting the right-hand helical thread. The left-hand helical cut can be configured to reduce a portion of a contact surface area of the right-hand helical thread and the sidewall.

In another form, a plating system for bone is provided in accordance with various aspects of the present teachings. The plating system can include a plate member and a fastener. The plate member can have a top surface, a bottom surface and can define a hole extending therebetween. The plate member hole can have a substantially spherical sidewall with a right-hand helical thread formed in the sidewall and a left-hand helical thread formed in the sidewall and intersecting the right-hand helical thread. The fastener can have a head and a threaded shank extending therefrom, where the head can include a right-hand helical thread formed on an outer surface thereof. The fastener can be configured to be received in the plate member hole in a first configuration whereby a longitudinal axis of the fastener is aligned with a longitudinal axis of the plate member hole, or in a second configuration whereby the longitudinal axis of the fastener is angled relative to the longitudinal axis of the plate member hole. The left-hand helical thread can be configured to reduce a portion of a contact surface area of the plate member hole right-hand helical thread and sidewall to facilitate receiving the fastener in the plate member hole in the second configuration in a locking manner.

In yet another form, a plating system for bone is provided in accordance with various aspects of the present teachings. The plating system can include a plate member having a top surface, a bottom surface and defining a hole extending between the top and bottom surfaces. At least a portion of the hole can have a tapered sidewall. A right-hand helical thread can be formed in the tapered sidewall of the hole, and a left-hand helical thread can be formed in the tapered sidewall of the hole and can intersect the right-hand helical thread. The left-hand helical cut can be configured to reduce a portion of a contact surface area of the right-hand helical thread and the tapered sidewall.

In another form, a variable angle locking system having a plate member and a fastener is provided in accordance with the present teachings. The plate member can include a threaded hole having a sidewall with a right-hand thread and a left-hand thread formed therein. The fastener can have a threaded head portion and an elongated shaft portion extending from the head portion. The threaded head portion can be configured to lockably mate with the threaded hole of the plate member at more than one angle relative to a horizontal plane defined by the plate member. The right-hand thread and the left-hand thread of the plate member hole can be configured to reduce a portion of a density or contact surface area of the sidewall.

In yet another form, a variable angle locking system having a bone plate and bone fastener is provided in accordance with the present teachings. The bone plate can include an upper surface and a lower surface and can define a hole extending therebetween. The hole can have a substantially spherical sidewall with a triple lead left-hand thread and a triple lead right-hand thread formed in the sidewall, where each of the triple lead right-hand and left-hand threads can include a variable pitch that increases in a direction from the upper surface to the lower surface. The bone fastener can have a threaded head portion and an elongated shaft portion extending from the head portion. The threaded head portion can include a double lead right hand thread formed on an outer surface thereof, a non-linearly tapered outer profile, and one or more flats forming a portion of the outer surface. The one or more flats can be adapted to reduce fastener application torque and to allow the head portion of the bone fastener to engage deeper into the bone plate as the head portion of the fastener is lockably mated with the threaded hole of the bone plate. The fastener can be configured to be received in the bone plate hole in a locking manner in an orientation whereby a longitudinal axis of the fastener is aligned with a longitudinal axis of the plate member hole and in various orientations whereby the longitudinal axis of the fastener is angled relative to the longitudinal axis of the plate member hole. The left-hand and right-hand triple lead helical threads can be configured to reduce a portion of a contact surface area of the bone plate threads and the sidewall to facilitate receiving the fastener in the plate member hole in various polyaxial orientations in the locking manner.

In another form, a variable angle locking system having a bone plate and a fastener is provided in accordance with the present teachings. The bone plate can have an upper surface and a lower surface and can define a hole extending therebetween. The hole can have a substantially spherical sidewall with a triple lead left-hand helical thread and a triple lead right-hand helical thread formed in the sidewall. Each of the triple lead right-hand and left-hand threads can have a variable pitch that increases in a direction from the upper surface to the lower surface. The bone fastener can have a threaded head portion and an elongated shaft portion extending from the head portion. The threaded head portion can have a double lead right-hand helical thread formed on an outer surface thereof, a non-linearly tapered outer profile, and one or more flats forming a portion of the outer surface. The one or more flats can be adapted to reduce fastener application torque and to allow the head portion of the bone fastener to engage deeper into the bone plate as the head portion of the fastener is lockably mated with the threaded hole of the bone plate. The fastener can be configured to be received in the bone plate hole in a locking manner in an orientation whereby a longitudinal axis of the fastener is aligned with a longitudinal axis of the bone plate hole and in various orientations whereby the longitudinal axis of the fastener is angled relative to the longitudinal axis of the bone plate hole. The left-hand and right-hand triple lead helical threads can be configured to reduce a portion of a contact surface area of the bone plate threads and the sidewall to facilitate receiving the fastener in the bone plate hole in various polyaxial orientations in the locking manner.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description, the appended claims and the following drawings. The drawings are for illustrative purposes only of selected embodiments and not all possible limitations, and are not intended to limit the scope of the present disclosure.

DESCRIPTION OF VARIOUS ASPECTS

Figure 1:
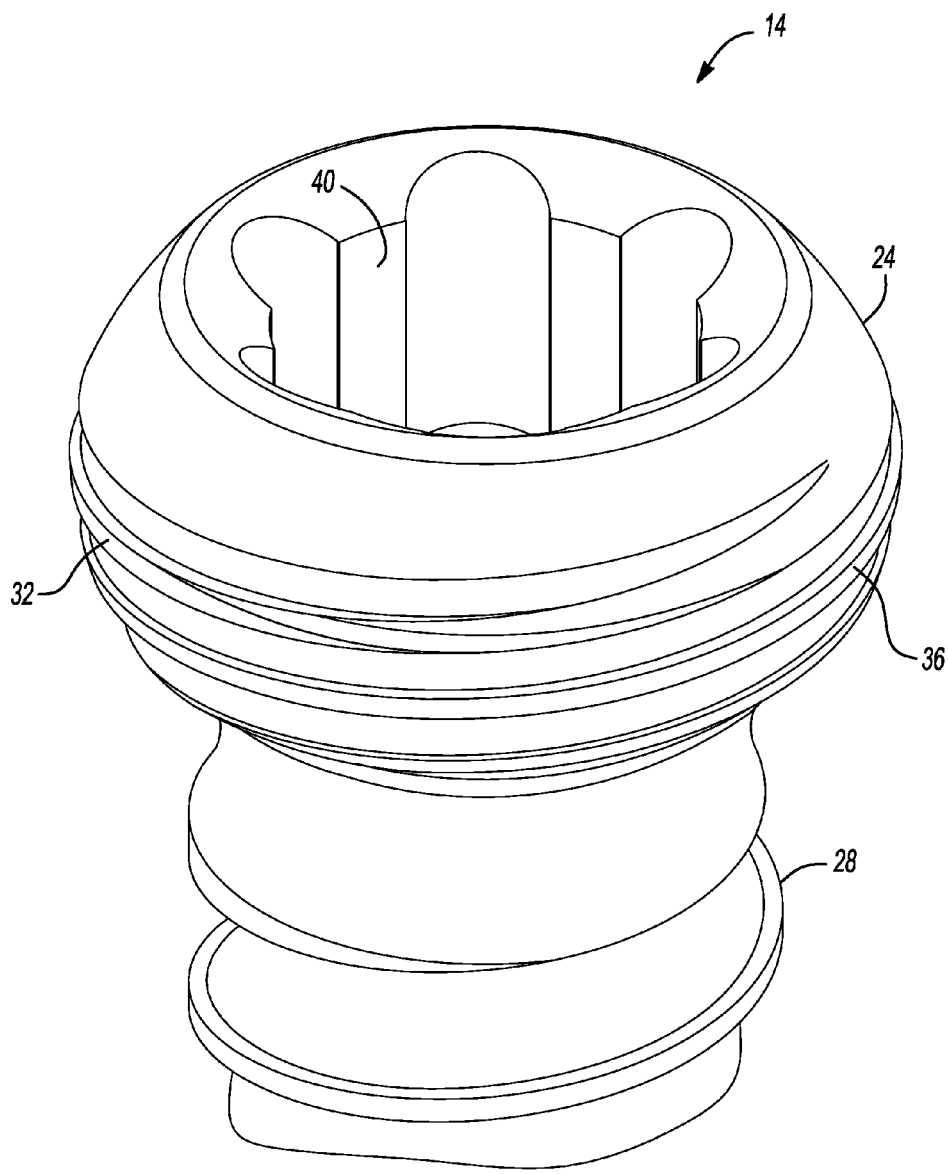
FIG. 1 is a partial perspective view of an exemplary bone screw illustrating a spherically shaped head with external threads in accordance with the present teachings.

The following description is merely exemplary in nature and is not intended to limit the present disclosure, its application, or uses. It should be understood that throughout the drawings, corresponding reference numerals indicate like or corresponding parts and features with the various elements in each view being drawn to scale.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

With general reference to FIGS. 1-11 of the drawings, a bone plating system constructed in accordance with the present teachings is illustrated and generally identified at reference character 10. The bone plating system 10 is illustrated to generally include a bone fastener or screw 14 and a bone plate 18.

With particular reference to FIG. 1, the bone screw 14 can include a spherically shaped head 24 and a threaded shank 28 extending therefrom. In one exemplary configuration, the spherically shaped head 24 can include a continuous helical protrusion or ridge 32 extending around the spherically shaped head 24. In an aspect of this configuration, the helical protrusion or ridge 32 can include an external helical thread 36. The external helical thread 36 can be in the form of a double lead right-hand helical thread. In one exemplary configuration, the double lead right-hand helical thread 36 can be formed with a pitch in the range of 1/48 inch to 1/64 inch. It should be appreciated, however, that other pitches can be utilized. In an aspect of this configuration, the pitch of the double lead right-hand helical thread 36 can be constant. For discussion purposes, the double lead right-hand external helical thread 36 extending around spherically shaped head 24 will be hereinafter referred to as the external spherical thread 36. Bone screw 14 can also include a driver engaging area, such as an internal recess 40 in bone screw head 24, configured to receive a driver or insertion tool (not shown) for advancing bone screw 14.

The bone plate 18 may be flat or may be contoured for specific applications in a manner well known in the art to conform to a bone. In one exemplary aspect, the bone plating system 10 can be used to stabilize a long bone, such as for example, a distal radius bone or a proximal humerus bone. It will become apparent to those skilled in the art, however, that the present teachings are also suitable for various other applications in which surgical repair of a bone with a plate and associated fastener is desired. As will be discussed in greater detail below, bone plate 18 can include a hole with a spherically threaded portion having a right-hand helical thread and a left-hand helical cut so as to facilitate locking the bone screw 14 in the bone plate hole in an on-axis or designed trajectory orientation as well as an off-axis or angulated orientation.

Figure 2:
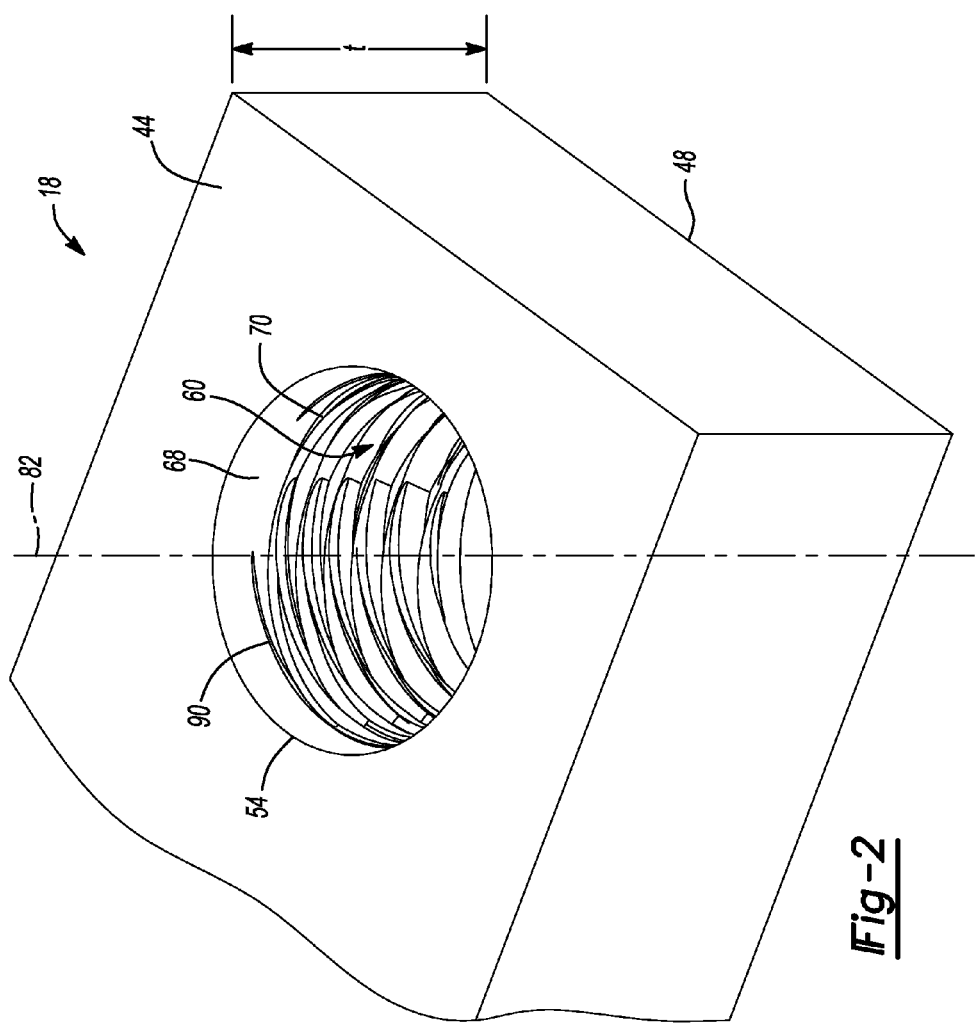
FIG. 2 is a perspective view of an exemplary bone plate illustrating a spherically shaped fastener hole with internal threading in accordance with the present teachings.

The bone plate 18 is generally shown in FIG. 2 to include an upper surface 44 and a lower surface 48. The bone plate 18 may be constructed of any suitable biocompatible material. One exemplary material is a titanium alloy such as Ti6Al4V. Other materials having acceptable strength characteristics, including but not limited to stainless steel, may also be utilized. In one exemplary aspect, the bone plate 18 defines a thickness t between the upper surface 44 and the lower surface 48. The thickness t may be constant throughout the bone plate 18 or may be variable. It should be readily apparent that the plate thickness t may vary according to material choices and/or strength requirements.

The bone plate 18 can define a hole 54 configured for polyaxial receipt and locking of bone screw 14. It should be appreciated that bone plate 18 can define a plurality of holes 54 for receiving a corresponding plurality of bone screws 14 for securing the bone plate 18 to a bone (not specifically shown). It will be understood that the particular number of holes 54 defined by the bone plate 18 and the specific configuration of holes 54 can vary (discussed below) within the scope of the present teachings and can largely depend on the intended application for the plating system 10. For purposes of illustration, however, the discussion will continue with reference to a single bone plate hole 54.

With additional reference to FIGS. 5-8 and continuing reference to FIGS. 1-2, the bone plate hole 54 will now be discussed in greater detail. Bone plate hole 54 can include an internal spherically threaded portion 60 forming a spherical contact surface area 64 of a spherical wall 66. In the exemplary configuration illustrated, an optional taper or lead-in chamfer 68 can be formed between the upper surface 44 and the spherically threaded portion 60. The spherically threaded portion 60 can include a first internal spherical thread 70 formed thereon. In an exemplary aspect of this configuration, the first internal spherical thread 70 can be formed so as to start on the taper 68. In one exemplary configuration, the spherical wall 66 can include a spherical shape in cross section that is complementary to the spherically shaped bone screw head 24.

In the exemplary configurations illustrated, the first internal spherical thread 70 can be a double lead right-hand helical thread formed in a helical manner in spherically threaded portion 60. The double lead right-hand spherical thread 70 can be sized and shaped to threadably receive the double lead external spherical thread 36 of spherical head 24 in a locking manner. In an aspect of this configuration, the double lead right-hand spherical thread 70 can also be formed with a pitch in the range of 1/48 inch to 1/64 inch corresponding to the selected pitch of external spherical thread 36 within the same range. Similar to the external spherical thread 36, the pitch of the double lead right-hand internal spherical thread 70 can also be constant. It should be appreciated, however, that while the following discussion will generally continue with reference to first internal spherical thread 70 being a double lead right-hand spherical thread, various other leads could be employed, such as a single lead or triple lead, for example.

Figure 3:
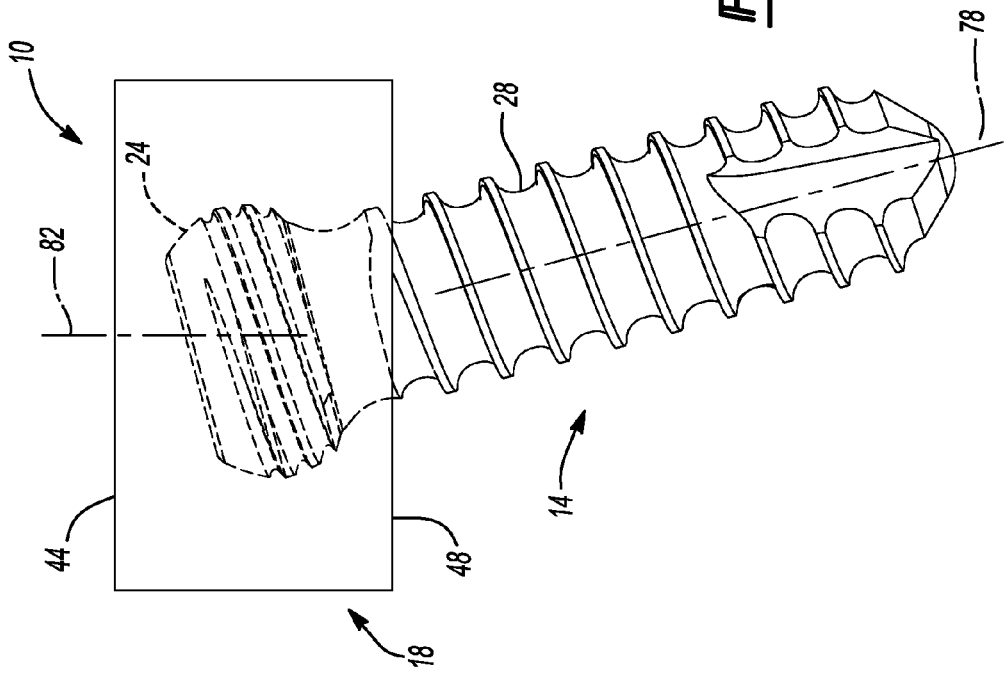
FIG. 3 is a view of the bone screw of FIG. 1 engaged with the bone plate hole of FIG. 2 where a longitudinal axis of the bone screw aligns with a longitudinal axis of the bone plate hole in accordance with the present teachings.
Figure 9:
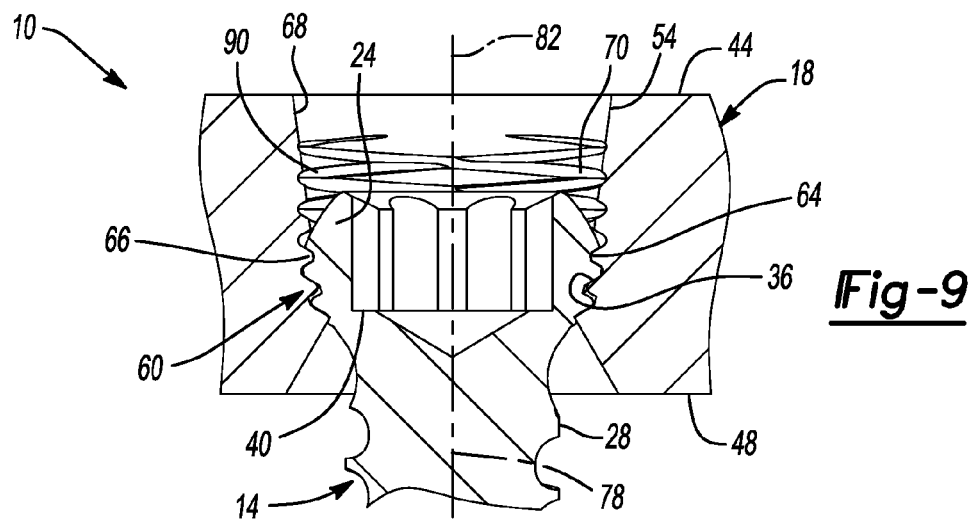
FIG. 9 is a cross-sectional view of the bone screw engaged with the spherically threaded bone plate hole of FIG. 7 where the longitudinal axes of the bone screw and bone plate are aligned in accordance with the present teachings.

FIGS. 3 and 9 illustrate the bone screw 14 being received in bone plate hole 54 in a locking manner in the on-axis orientation where a longitudinal axis 78 of bone screw 14 is in alignment with a longitudinal axis 82 of bone plate hole 54. In this configuration, the external spherical threads 36 of the spherical head 24 can threadably engage the right-hand spherical threads 70 of bone plate hole 54 in a locking manner.

With continuing reference to FIGS. 5-8, the bone plate hole 54 can include a left-hand helical cut 90 in the spherical wall 66 of spherically threaded portion 60 of bone plate hole 54. As will be discussed in greater detail below, the left-hand helical cut 90 can be used to reduce an amount or density of the spherical contact surface area 64 in spherically threaded portion 60, including the right-hand spherical threads 70, that is available for threadable engagement with external spherical threads 36 of spherical head 24. In one exemplary configuration, the left-hand helical cut 90 can reduce the density of a minor-diameter of the right-hand spherical threads 70 by removing a portion of the threads 70 as the left-hand helical cut 90 intersects the right-hand spherical threads 70. As will also be discussed below, the left-hand helical cut 90 can be configured in various forms (e.g., various combinations of pitch, cut depth, number of leads, etc.) to vary the density of the right-hand spherical threads 70 and associated spherical contact surface area 64, as well as a pattern and location of the density.

In one exemplary aspect, the left-hand helical cut 90 can be a continuous spherical thread formed in a helical manner in the spherically threaded portion 60 so as to intersect the right-hand spherical threads 70 at a desired angle relative to threads 70. It should be appreciated, however, that while the following discussion will continue with reference to the left-hand helical cut 90 being a left-hand spherical thread, the left-hand spherical thread 90 can be provided in various forms, such as a protrusion or ridge.

As briefly discussed above, the left-hand spherical thread 90 can be formed in bone plate hole 54 in various predetermined configurations to vary an amount of the left-hand spherical thread 90 that intersects the right-hand spherical thread 70 so as to variably reduce a density or remaining portion of spherical thread 70 and adjacent spherical contact surface area 64 available for threadably engaging the external spherical threads 36 of bone screw head 24. Reducing the density can provide for facilitating the bone screw 14 to be threadably received and locked in the bone plate hole 54 in various polyaxial orientations where the longitudinal axis 78 of the bone screw 14 is angled relative to the longitudinal axis 82 of the bone plate hole 54, as generally shown in FIGS. 4 and 9-11. The reduced density can provide for the external spherical threads 36 of bone screw 14 to more easily cut into or tap the spherical contact surface area 64, including right-hand spherical threads 70, at a desired off-axis angle of the bone screw 14.

By using the left-hand spherical threads 90 to reduce the density of the right-hand internal spherical threads 70 and the overall spherical contact surface area 64 of spherically threaded portion 60, the same material can be used for both the bone plate 18 and the bone screw 14. This can reduce cost and complexity as compared to other plating systems that require using various softer materials for the bone plate versus the bone screw to facilitate polyaxial receipt and locking of the bone screw in the bone plate. In other words, the left-hand spherical threads 90 can be varied to reduce the density of the spherical contact surface area 64 for various different applications instead of having to use multiple different softer materials for bone plate 18 for the different applications.

Figure 5:
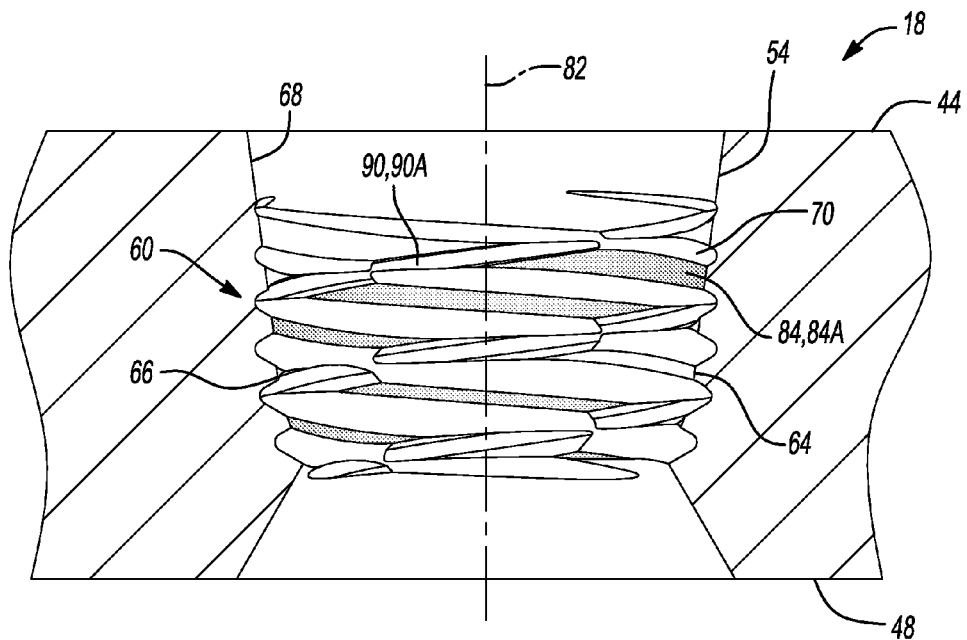
FIG. 5 is a cross-sectional view of the bone plate hole illustrating an exemplary configuration of right-hand spherical threads and left-hand spherical threads in accordance with the present teachings.

For example, FIG. 5 illustrates one exemplary configuration where the left-hand spherical threads 90 are formed in a configuration 90A in spherically threaded portion 60 of bone plate 18. The configuration 90A can include a double lead helical cut at a pitch of two times the pitch of the right-hand spherical threads 70. The left-hand spherical thread configuration 90A can intersect the right-hand spherical threads 70 and adjacent spherical contact surface area 64 thereby removing a portion of right-hand spherical threads 70 and spherical contact surface area 64 and thus reducing a density of the overall spherical contact surface area to a first density 84A shown in FIG. 5.

Figure 6:
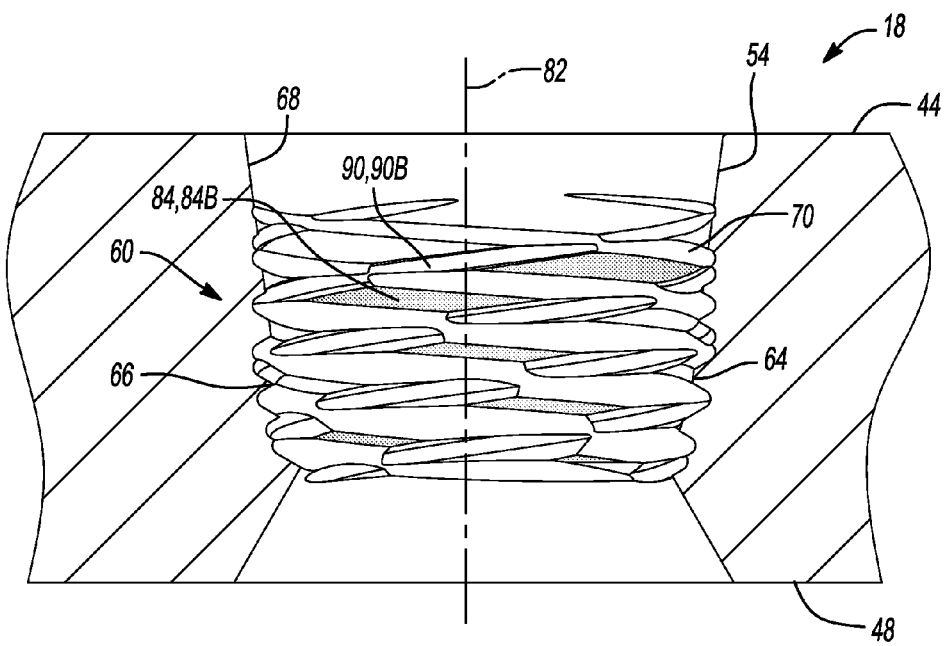
FIG. 6 is a cross-sectional view of the bone plate hole illustrating another exemplary configuration of right-hand spherical threads and left-hand spherical threads in accordance with the present teachings.

FIG. 6 illustrates another example of the density reduction where a configuration 90B of the left-hand spherical threads 90 is formed in spherically threaded portion 60 to reduce the density of the overall spherical contact surface area to a second density 84B. In this example, left-hand spherical thread configuration 90B can include a triple lead left-hand helically cut spherical thread at a pitch of two times the pitch of the right-hand spherical threads 70. As can be seen in this exemplary configuration, the second density 84B is less than the first density 84A of FIG. 5 as a result of the increased number of leads of the left-hand spherical thread configuration 90B.

Figure 7:
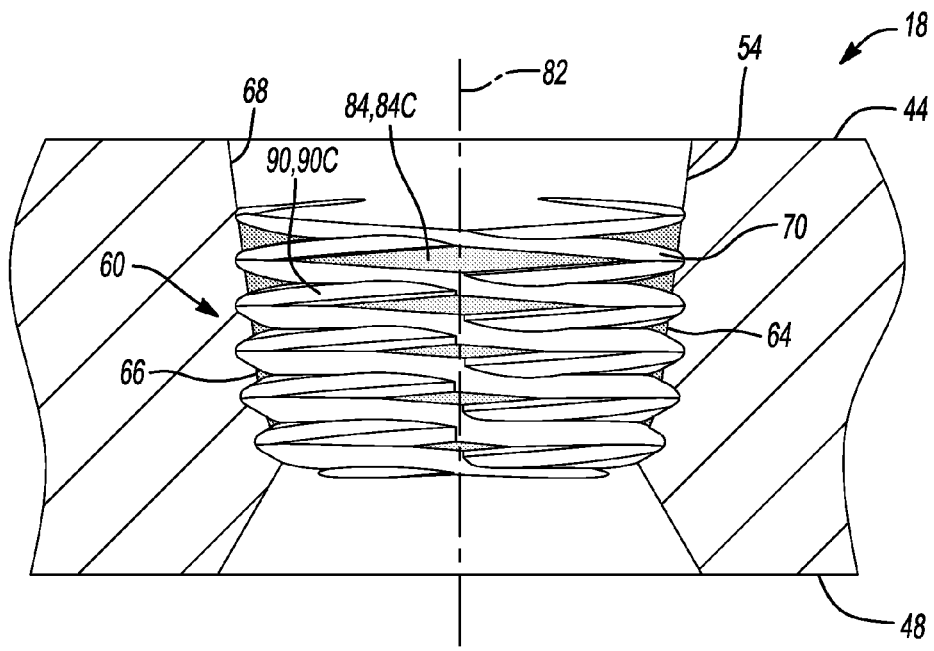
FIG. 7 is a cross-sectional view of the bone plate hole illustrating another exemplary configuration of right-hand spherical threads and left-hand spherical threads in accordance with the present teachings.

FIG. 7 illustrates another example of density reduction of the overall spherical contact surface area 64, including right and spherical threads 70, where a configuration 90C of left-hand spherical threads 90 is formed in the spherically threaded portion 60. In this exemplary configuration, the left-hand thread configuration 90C is formed with a double lead helical cut at the same pitch as the right-hand spherical threads 70. As can be seen in FIG. 7, the left-hand spherical thread configuration 90C intersects the right-hand spherical threads 70 at a smaller acute angle than configurations 90A and 90B discussed above. As a result, a larger portion or percentage of the right-hand spherical threads 70 and overall spherical contact surface area 64 can be removed with this configuration resulting in a third density 84C of the overall spherical contact surface area 64 that is less than densities 84A and 84B discussed above.

As can also be seen in FIG. 7, the left-hand spherical threads 90 can be formed in spherically threaded portion 60 with a configuration, such as configuration 90C, to specifically position the density (third density 84C in this example) in a specific circumferential orientation in bone plate hole 54. In this exemplary configuration, the left-hand spherical thread configuration 90C has been formulated to orientate third density 84C in four discrete quadrants (three illustrated) circumferentially around hole 54, as shown in FIG. 7.

It should be appreciated, however, that the number of leads and pitch of the left-hand spherical threads can be varied to form various resulting densities and density orientations as may be desired for a specific bone plating system application and/or manufacturing technique. In this regard, for example, the specific placement and symmetry of the third density 84C in FIG. 7 can be contrasted against the generally random or non-symmetric placement of the first and second densities 84A, 84B in respective FIGS. 5 and 6.

Figure 8:
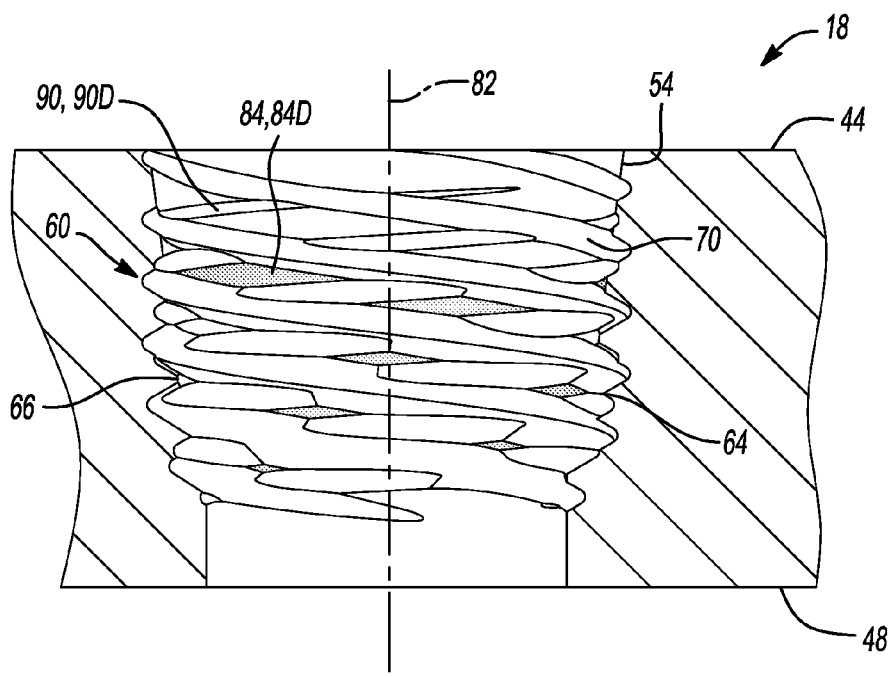
FIG. 8 is a cross-sectional view of the bone plate hole illustrating another exemplary configuration of right-hand spherical threads and left-hand spherical threads in accordance with the present teachings.

FIG. 8 illustrates another example of the manipulation of the left-hand spherical threads 90 to alter the density of the overall spherical contact surface area 64. In this exemplary configuration, a depth of the left-hand spherical cut has been increased such that more of the spherical contact surface area 64 can be removed resulting in a fourth density 84D that is less than the densities 84A-84C discussed above.

Figure 4:
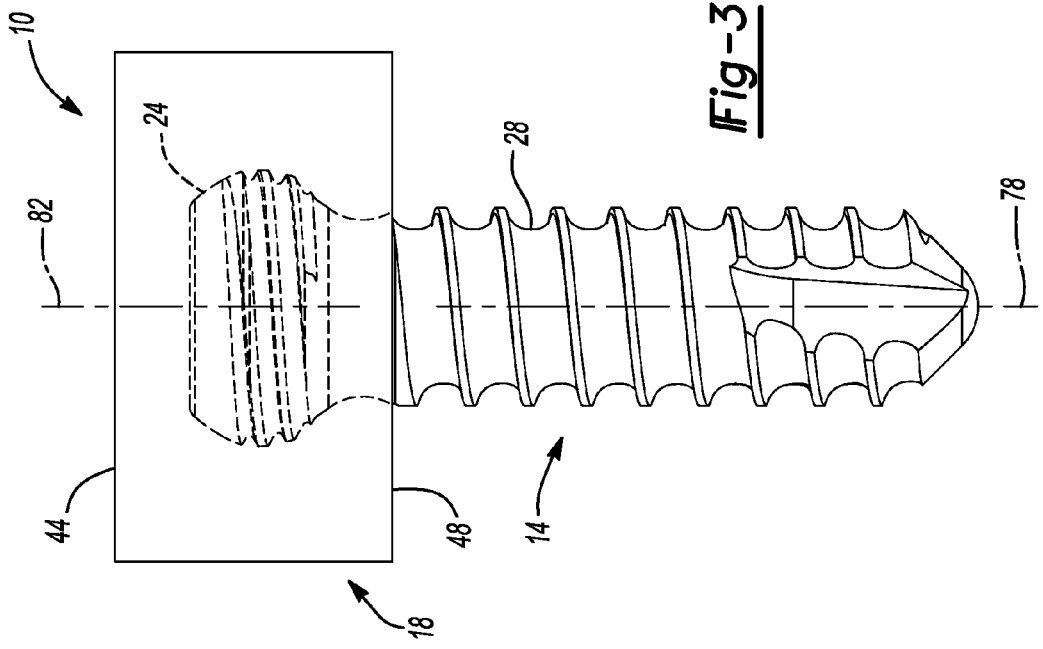
FIG. 4 is a view of the bone screw engaged with the bone plate hole and angulated from the orientation illustrated in FIG. 3 in accordance with the present teachings.
Figure 10:
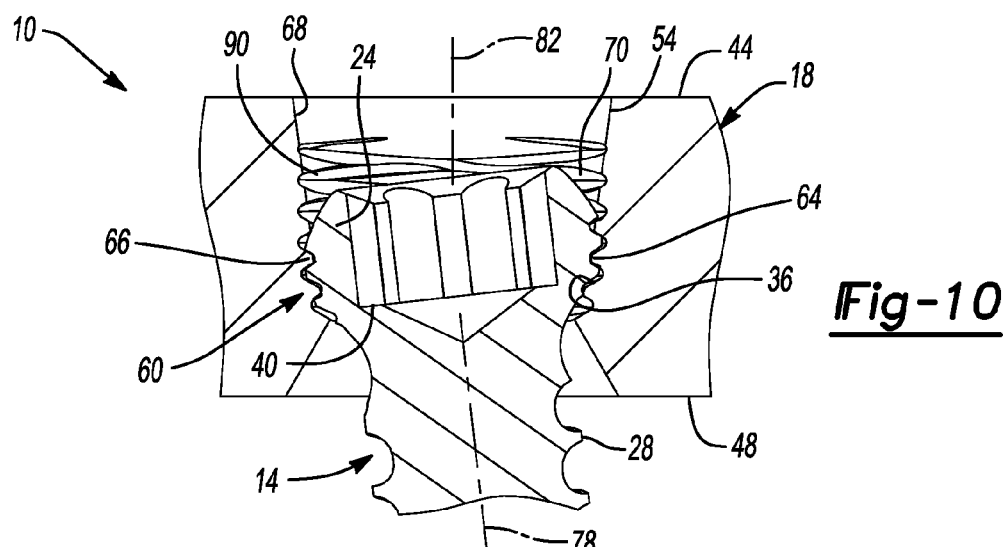
FIG. 10 is a cross-sectional view of the bone screw engaged with the spherically threaded bone plate hole of FIG. 7 where the longitudinal axis of the bone screw is angulated relative to the longitudinal axis of the bone plate hole in accordance with the present teachings.
Figure 11:
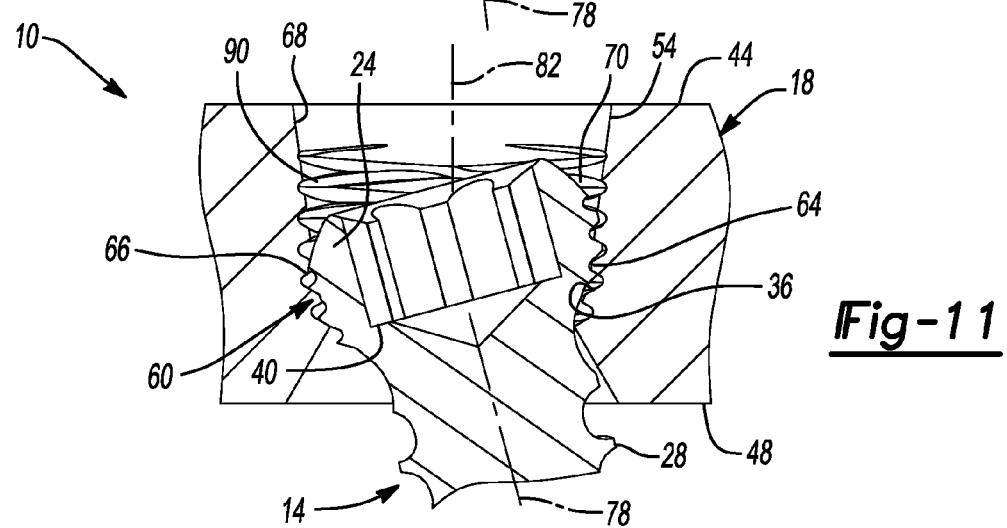
FIG. 11 is a cross-sectional view of the bone screw engaged with the spherically threaded bone plate hole of FIG. 7 where the longitudinal axis of the bone screw is angulated relative to the longitudinal axis of the bone plate hole in accordance with the present teachings.

In reducing the density of the spherical contact surface area 64 of the spherically threaded portion 60, the external spherical threads 36 of bone screw 14 can more easily cut or tap into the spherical contact surface area 64 of spherical wall 66 in various angled orientations relative to the on-axis designed trajectory, such as shown in FIGS. 4, 10 and 11. By varying the pitch, cut depth and number of leads of left-hand spherical threads 90, the density 84 of the spherical contact surface area 64 can be variably reduced to provide for a desired amount and location of a remaining amount of spherical contact surface area 64 to facilitate receiving and locking bone screw 14 in various off-axis or angulated orientations. In one exemplary aspect, when a plate material is selected having a relatively high hardness, such as stainless steel, more density reduction may be required via the left-hand spherical threads 90 to facilitate screw 14 tapping into the spherical contact surface area 64 in an angulated off-axis orientation. In this exemplary aspect, the left-hand spherical thread configurations 90C or 90D can be used, for example, to provide for the greater density reduction.

FIGS. 9-11 illustrate three general examples of bone screw 14 being threadably received in bone plate hole 54. As discussed above, bone screw 14 can be received in bone plate hole 54 in the designed trajectory where the longitudinal axis 78 of bone screw 14 is aligned with the longitudinal axis 82 of bone plate hole 54 (FIG. 9), or in the off-axis or angled orientation where longitudinal axis 78 is angulated relative to longitudinal axis 82 (FIGS. 10 and 11).

In the designed trajectory configuration shown in FIG. 9 (as well as generally in FIG. 3), the right-hand spherical threads 36 can threadably engage the corresponding right-hand spherical threads 70 in bone plate hole 54 in a locking manner. In addition, bone plate hole 54 can also facilitate receipt and locking of bone screw 14 at various angles relative to the longitudinal axis 82 of bone plate hole 54, such as at an exemplary 6.5 degree angled orientation shown in FIG. 10 and an exemplary 15 degree angled orientation shown in FIG. 11. As can be seen in FIGS. 10 and 11, the spherical shape of bone screw head 24 and the spherical contact surface area 64 of spherical wall 66 can facilitate greater surface contact of external threads 36 of bone screw 14 with at least a portion of right-hand spherical threads 70 and spherical contact surface area 64 when bone screw 14 is received in bone plate hole 54 at an angled orientation relative to longitudinal axis 82.

Figure 12:
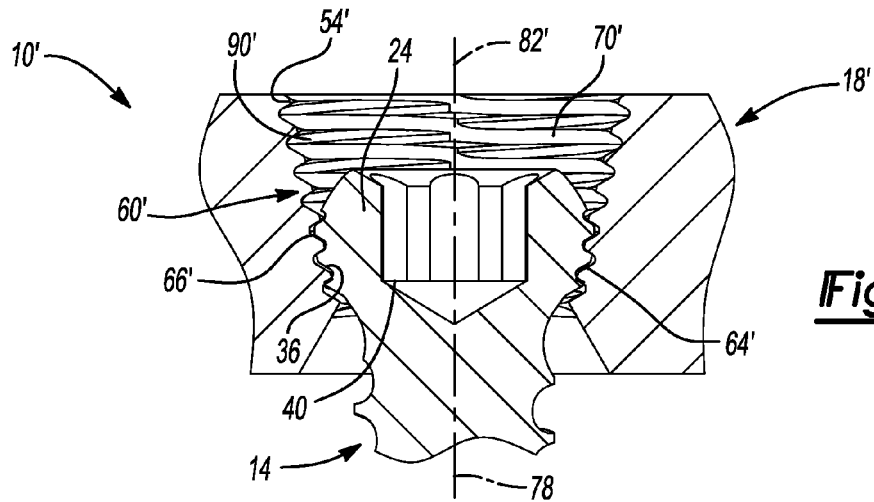
FIG. 12 is a cross-sectional view of the bone screw threadably engaged with an exemplary tapered bone plate hole where the longitudinal axis of the bone screw and bone plate hole are aligned in accordance with the present teachings.
Figure 13:
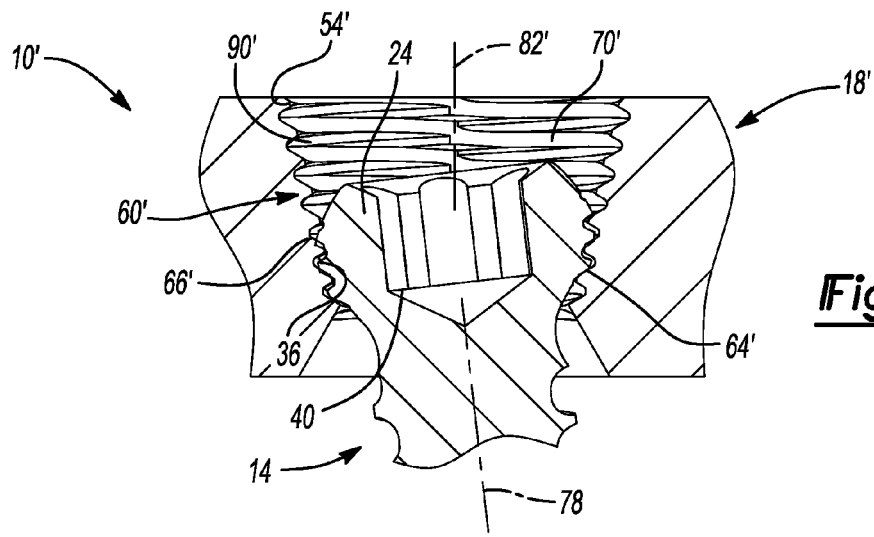
FIG. 13 is a cross-sectional view of the bone screw threadably engaged with an exemplary tapered bone plate hole where the longitudinal axis of the bone screw is angulated relative to the longitudinal axis of the bone plate hole in accordance with the present teachings.
Figure 14:
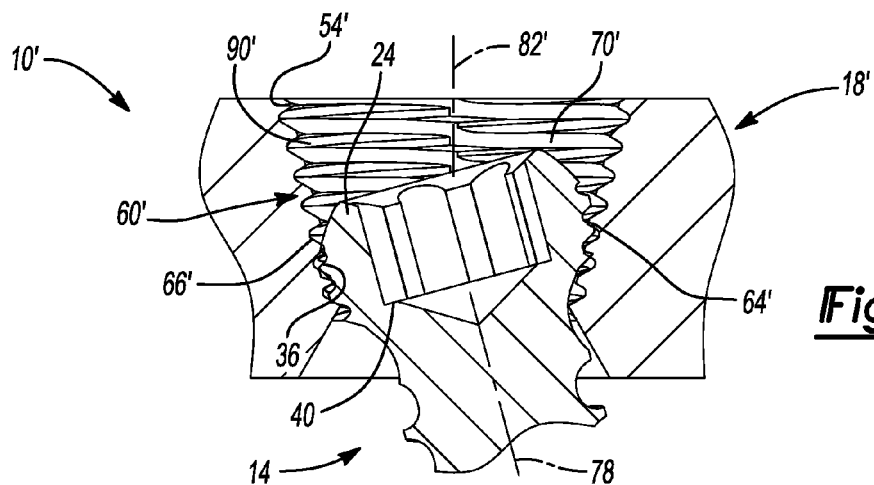
FIG. 14 is a cross-sectional view of the bone screw threadably engaged with an exemplary tapered bone plate hole where the longitudinal axis of the bone screw is angulated relative to the longitudinal axis of the bone plate hole in accordance with the present teachings.

Turning now to FIGS. 12-14, another exemplary bone plating system 10' is shown in accordance with the present teachings. Bone plating system 10' can be similar to bone plating system 10 such that like reference numerals refer to like features and only differences will be discussed in detail. Bone plating system 10' can include spherically threaded bone screw 14 and an associated bone plate 18' having a tapered hole 54' with a tapered sidewall 66'. Tapered hole 54' can include a threaded portion 60' having right-hand internal helical threads 70' and a left-hand helical cut 90', similar to spherical bone plate hole 54 discussed above. In this regard, bone plate hole 54' can include similar variations of the right-hand helical threads 70' and left-hand helical cut or threads 90' discussed above for bone plate hole 54 so as to reduce an amount or density of a contact surface area 64' of tapered sidewall 66'.

FIGS. 12-14 illustrate three general examples of bone screw 14 being threadably received in tapered bone plate hole 54' similar to FIGS. 9-11 discussed above. In the exemplary configurations shown in FIGS. 12-14, bone screw 14 includes the double-lead right-hand external spherical threads 36, and the tapered bone plate hole 54' includes a double lead right-hand helical thread configuration 70' as well as a double lead left-hand cut or thread configuration 90'. In this exemplary configuration, the pitch of the right-hand helical thread configuration 70' and the left-hand cut or thread configuration 90' are the same.

In the designed trajectory configuration shown in FIG. 12, the external spherical threads 36 can threadably engage the corresponding right-hand helical threads 70' in tapered bone plate hole 54' in a locking manner. In addition, bone plate hole 54' can also facilitate receipt and locking of bone screw 14 at various angles relative to the longitudinal axis 82' of bone plate hole 54', such as at an exemplary 6.5 degree angled orientation shown in FIG. 13 and an exemplary 15 degree angled orientation shown in FIG. 14. As can be seen in FIGS. 13 and 14, the spherical shape of bone screw head 24 can facilitate greater surface contact of external threads 36 of bone screw 14 with at least a portion of right-hand helical threads 70' of tapered sidewall 66' when bone screw 14 is received in bone plate hole 54' at an angled orientation relative to longitudinal axis 82'.

Turning now to FIGS. 15-25 and with continuing reference to FIGS. 1 through 14, a variable angle locking bone plating system constructed in accordance with the present teachings is illustrated and generally identified at reference numeral 10". Bone plating system 10" can be similar to bone plating system 10 such that only differences will be discussed in detail and like reference numerals refer to like or similar components or features.

Figure 15:
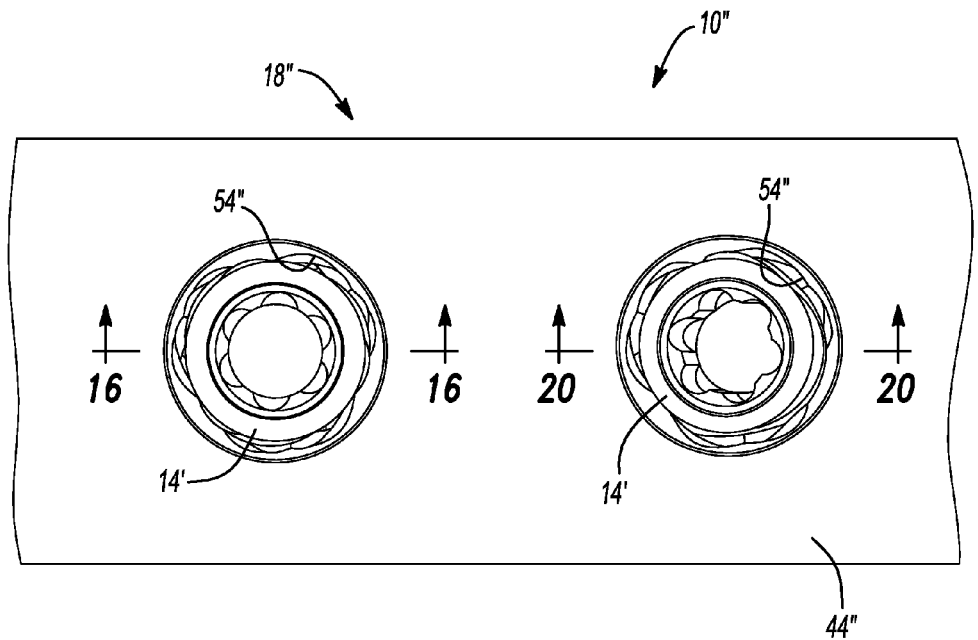
FIG. 15 is a partial top view of an exemplary bone plating system having variable angle locking screws attached to the bone plate in accordance with the present teachings.

Similar to bone plate system 10, the bone plating system 10" can generally include a bone screw 14' and a bone plate 18". The bone plate 18" may be flat or may be contoured for specific applications in a manner well known in the art to conform to a bone. The bone plate 18" is generally shown to include an upper surface 44" and a lower surface 48". In one aspect, the bone plate 18" can define a thickness t between the upper surface 44" and the lower surface 48". The thickness t may be constant throughout the bone plate 18" or may be variable. In accordance with certain illustrative aspects of the present teachings, the bone plate 18" can define one or more holes 54" for receiving bone screws 14' for securing the bone plate 18" to bodily tissue such as, without limitation, bone (not specifically shown). For purposes of illustration, the bone plate 18" is shown in FIG. 15 to include two holes 54"; however, it should be understood and appreciated herein that the particular number of holes defined by the plate member, as well as the specific types of holes used, may vary within the scope of the present teachings. To this end, it should also be appreciated herein that this variability can largely depend on the intended application for the plating system 10".

Figure 16:
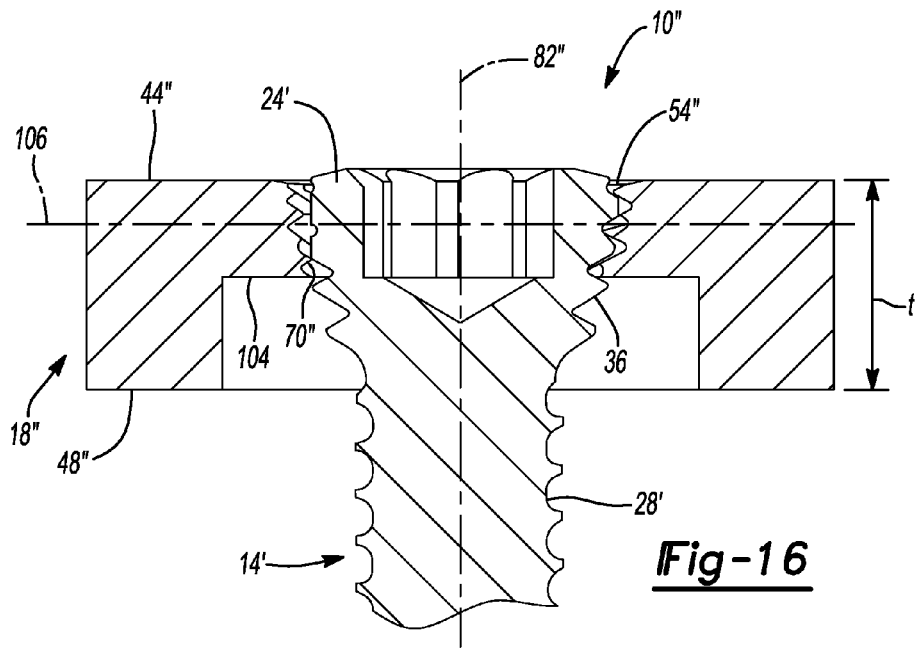
FIG. 16 is a cross-sectional view of a portion of the plating system of FIG. 1 along the line 16-16 in accordance with the present teachings.

As can be seen in FIG. 16, to mount the bone plate 18" to bone, a bone screw or similar fastener 14' is threaded through a hole 54" that extends between the upper surface 44" and the lower surface 48" of the bone plate 18". In this embodiment, each hole 54" of the plate 18" can be threaded (i.e., includes at least one ridge 70" extending completely about an inner circumference).

As will be explained in more detail below, the ridges 70" can be configured to cooperate with a spherically shaped head 24' of bone screw 14'. For example, and with specific reference to FIGS. 16 and 17, the bone screw 14' can include a spherically shaped head 24' having the double lead spherical thread 36 for engaging the ridges 70". While this specific embodiment describes the head 24' of the bone screw 14' as having a spherical shape, it should be understood and appreciated herein that the shape of the head does not need to be spherical in nature (e.g., the shape of the head can alternatively be conical, conical-spherical, or the like without straying from the teachings of the present invention). Engagement of the head 24' with the ridges 70" functions to orient the bone screw 14' relative to the bone plate 18" and to fix the bone screw 14' relative to the bone plate 18". In accordance with certain aspects of the present invention, the ridges 70" of the threaded hole 54" commence at the upper surface 44" of the bone plate 18" and terminate before reaching the lower surface 48". According to this illustrative aspect of the present invention, at the location where the ridges 70" terminate, a cavity 104, defined partially by the underside (lower surface) of the bone plate 18", can be formed.

Figure 20:
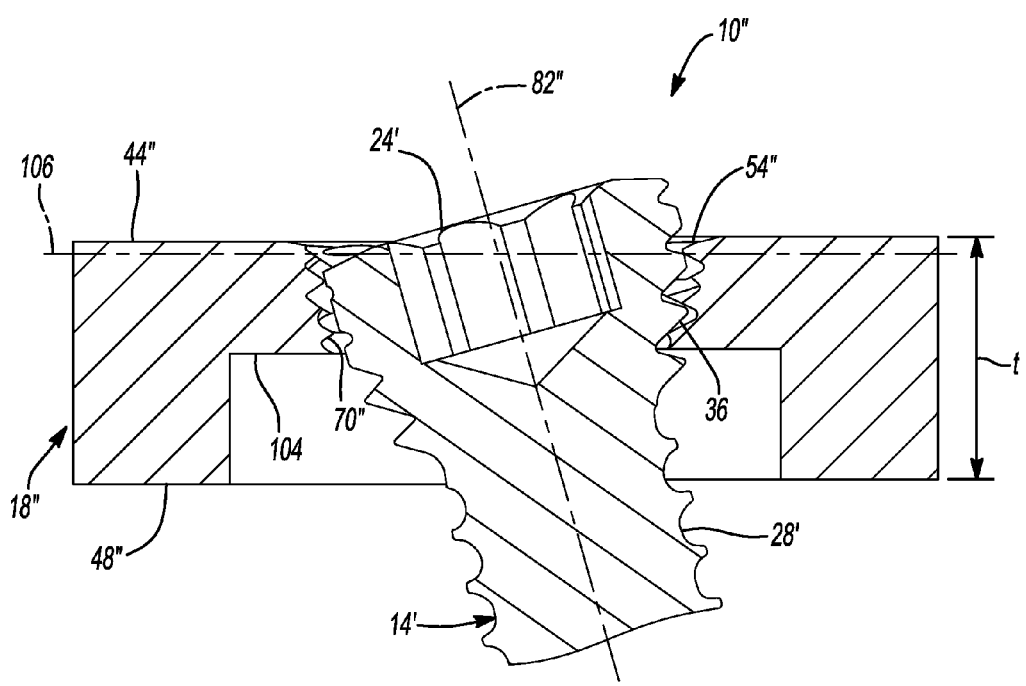
FIG. 20 is a cross-sectional view of a portion of the plating system of FIG. 15 along line 20-20 in accordance with the present teachings.

With particular reference to FIG. 20, when the bone screw 14' is secured to the bone plate 18" at an angle non-perpendicular to the horizontal plane 106 defined by the bone plate 18", the formed cavity 104 provides a space for allowing the shaft or shank 28' of the bone screw 14' to be angularly repositioned without encountering resistance from any surfaces of the bone plate 18". It should be understood and appreciated herein that those of skill in the relevant art would readily understand that the dimensions of the cavity 104 can be adjusted as necessary to accommodate the specific angular variability desired for securing the bone screw to the plate member, as well as in light of the specific application to which the inventive process is being applied. Accordingly, the present teachings are not intended to be limited herein.

Figure 21:
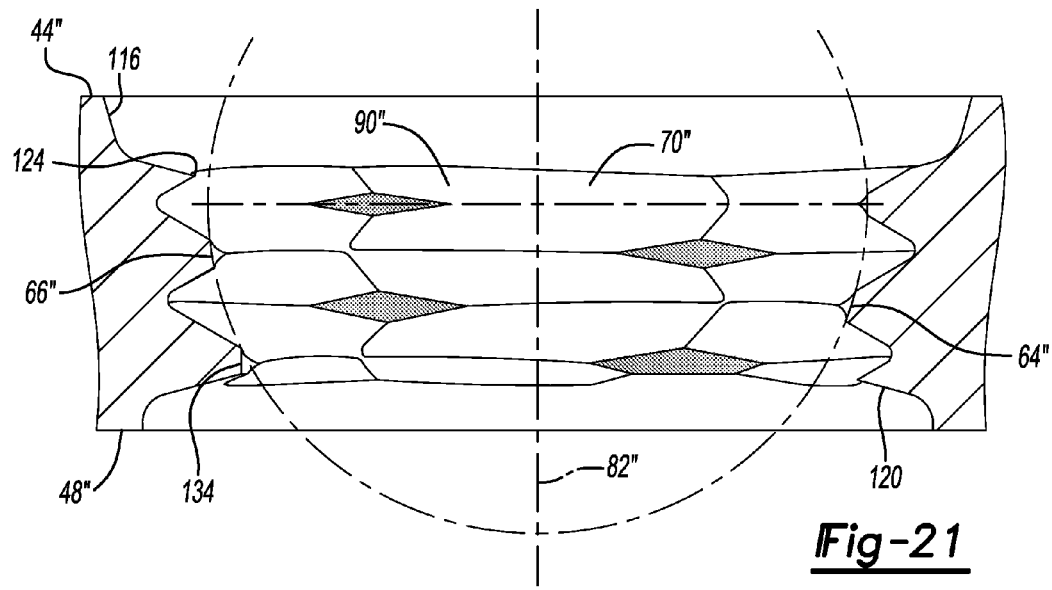
FIG. 21 is a cross-sectional view of an exemplary bone plate hole configuration of the plating system of FIG. 15 in accordance with the present teachings.
Figure 22:
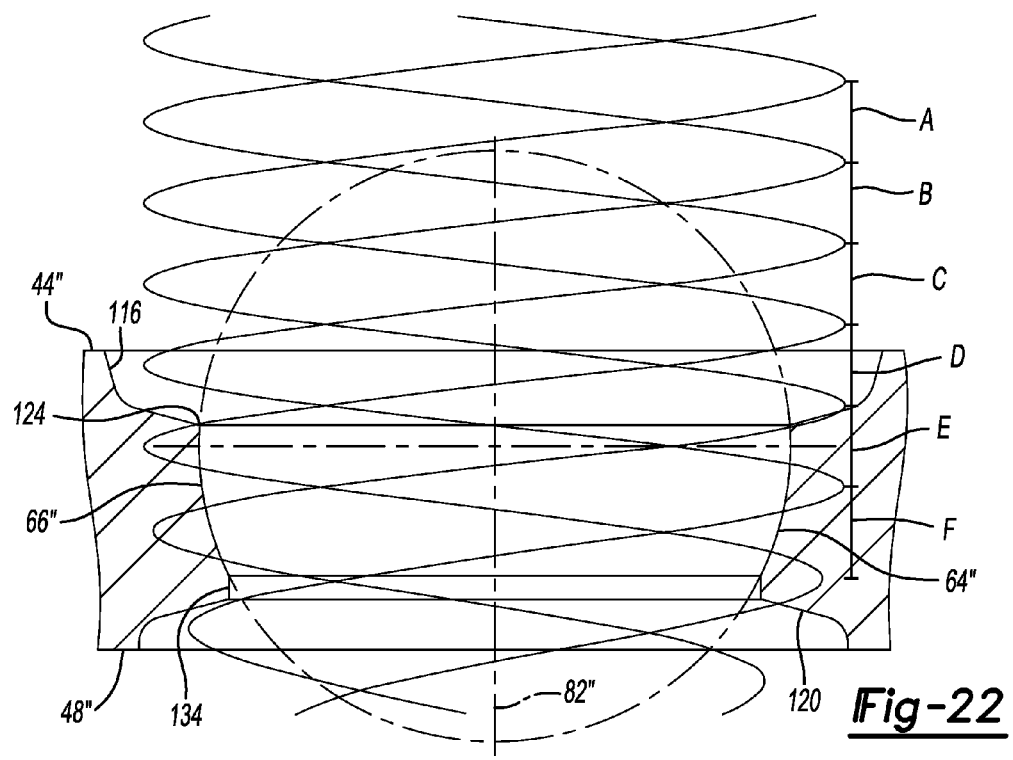
FIG. 22 is a schematic view of the bone plate hole of FIG. 21 illustrating left-hand and right-hand thread paths without the threads being cut into the bone plate hole in accordance with the present teachings.

In one exemplary configuration shown in FIGS. 21-25, bone plate 18" can include an upper chamfer 116 and a lower chamfer 120. Upper chamfer 116 can extend from the upper surface 44" to an upper end 124 of spherical wall 66" (shown here without threads for illustrative purposes only) and lower chamfer or undercut 120 can extend from a lower end 134 of spherical wall 66" to lower surface 48". Chamfers 116, 120 can be formed at various angles, include a 150 degree angle as shown in FIGS. 21-22. The spherical wall 66", as shown for example in FIG. 22 without threads, provides a visual indication of shape of the spherical wall 66" before the hole is threaded (i.e., the surface that forms the minor diameter of the threads cut into hole 54").

Figure 17:
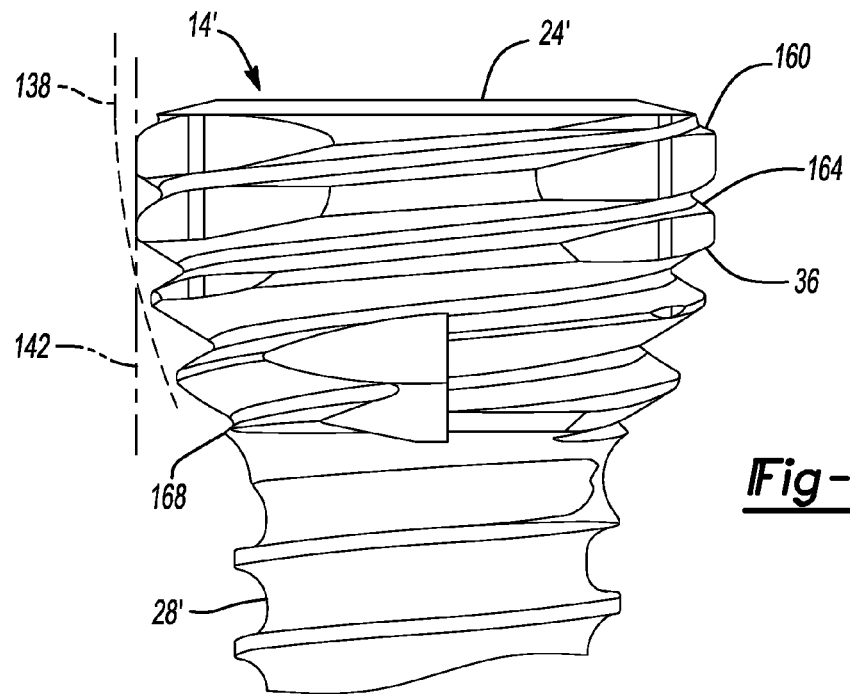
FIG. 17 is a profile view of a head portion of an exemplary variable angle bone fastener in accordance with the present teachings.
Figure 18:
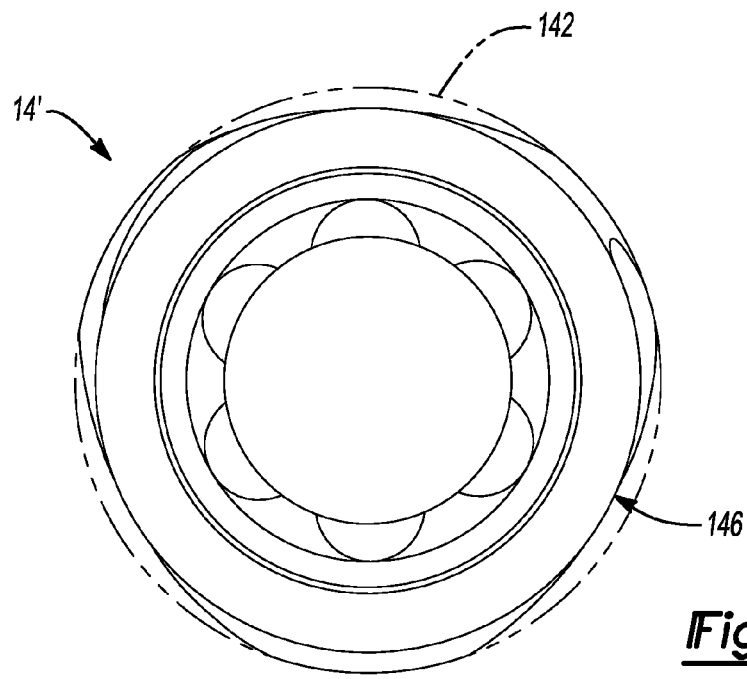
FIGS. 18 and 19 are top views of the exemplary bone fastener of FIG. 17 in accordance with the present teachings.
Figure 19:
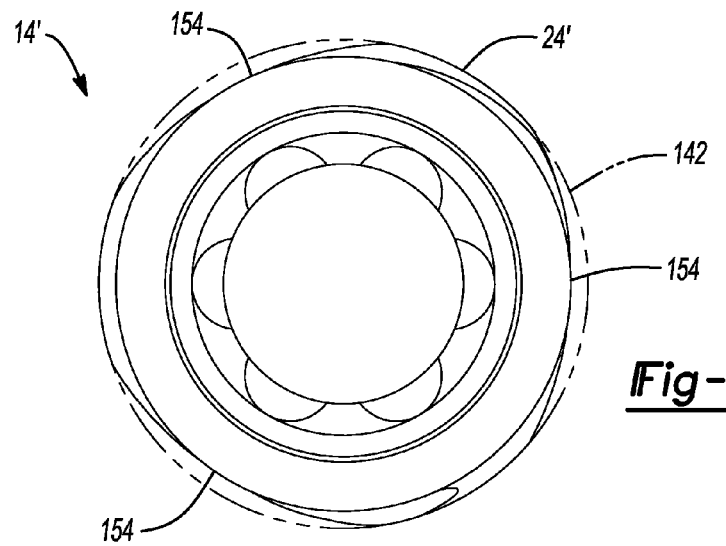

As can be appreciated from FIGS. 17-18, in accordance with various aspects of the present teachings, the head 24' of the bone screw 14' can include a non-linearly tapered outer profile 138. In accordance with this aspect, the outer screw head profile can gradually deviate from a spherical form and an outside diameter 142 (the maximum deviation from the outside diameter 142 is indicated by reference numeral 146 of FIG. 18). By utilizing a non-linearly tapered head profile 138, it is possible to gradually increase material interference during variable angle locking applications, which in turn, allows the screw head 24' to engage deeper with the bone plate 18", as well as can help to eliminate metal burr created from the bone screw 14'.

In addition to having the non-linearly tapered outer profile 138, in accordance with certain aspects of the present teachings, the bone screw head 24' can also include one or more cuts or flats 154 to reduce the screw application torque and allow the screw head to engage deeper into the bone plate 18". An illustrative embodiment having three flats 154 cut into screw head 24' can be seen with reference to FIG. 19. By adding one or more flats 154 to the screw head 24', the strength of the variable angle locking plating system 10 can be increased by allowing the screw head to further engage the bone plate 18" (e.g., much like a "thread-forming" feature).

As shown in FIG. 17, other features that may also be added to the bone screw head 24' in accordance with various illustrative embodiments of the present teachings include rounded edges 160 between the back surface 164 and the profile of the screw head 24' and one or more tapping features 168 near the shaft portion 28' of the screw 14'. When a portion of the screw head 24' is left above the upper surface 44" of the bone plate 18" as a result of the bone screw 14' being secured at an extreme angle, the addition of round edges 160 can help to minimize the upper surface 44" of the plating system 10 from having any sharp edges that may cause soft tissue irritation. Moreover, the addition of one or more taps 168 helps ensure that the bone screw 14' and bone plate 18" are fully engaged (i.e., the screw is driven further into bone) during a fixation process by allowing the screw 14' to sit low enough relative to the bone plate 18".

As should be understood and appreciated herein, the locking screw 14' of the present teachings can be utilized with various variable angle locking assemblies in various polyaxial orientations, as generally discussed above with reference to FIGS. 4, 10-11 and 13-14. To achieve such angular variability, and with particular reference to FIGS. 21-25, the hole 54" can include a triple lead right-hand helical cut 70" and a triple lead left-hand helical cut 90" formed in the spherical wall 66" in a similar manner as discussed above. In one exemplary configuration, the right-hand helical cut 70" and the left-hand helical cut 90" can be right-hand and left-hand helical threads, respectively, as shown for example in FIGS. 21 and 23. Similar to the configuration discussed above in FIGS. 1-14, the combination of the right-hand and left-hand helical or spherical threads 70", 90" in hole 54" can reduce the amount of density 84" or the contact surface area 64" of the sidewall 66" and the contact surface area of the threads 70", 90", as will be discussed in greater detail below.

Figure 23:
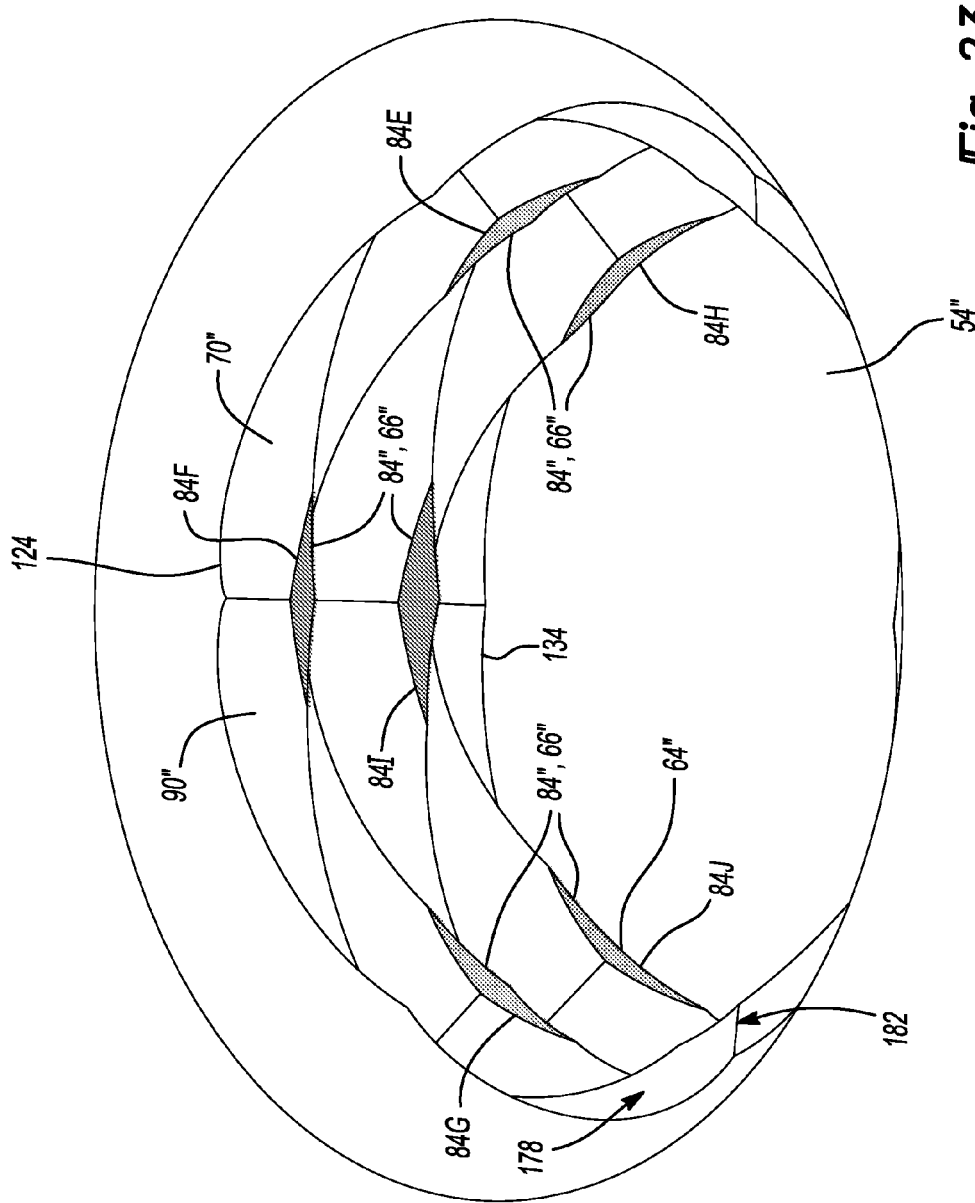
FIG. 23 is a partial perspective view of the bone plate hole of the plating system of FIG. 15 in accordance with the present teachings.

With particular reference to FIGS. 22 and 23, the right-hand and left-hand helical threads 70", 90" can include the same pitch (e.g., they can be mirror images of each other) and can be formed about or substantially about central longitudinal axis 82". In an exemplary configuration, the pitch can vary from the top of hole 54" to the bottom of hole 54". In this particular configuration, the pitch can increase from the upper end 124 of hole 54" to the lower end 134 of hole 54", as shown for example in FIG. 22. As can be seen in this figure, the pitch increases from A to E, where A and B are for illustrative purposes as they are above the hole formed in bone plate 18". It should be appreciated that the upper and lower ends of hole 54" can be flush with the respective upper and lower surfaces 44", 48", or spaced apart therefrom as discussed above in connection with chamfers 116, 120.

The triple lead threads 70", 90" combined with the variable pitch increasing from the upper end to the lower end of hole 54" can provide for varying density 84" or the contact surface area 64" of sidewall 66", as shown for example in FIG. 23. The varying density, combined with the density reduction of the thread contact surface area through use of both the right-hand and left-hand triple lead threads 70", 90" can provide for enhanced polyaxial locking capabilities in hole 54". In particular, such a combination of thread features in hole 54" can provide for the external double lead threads 36 of screw 14' to more easily cut into or tap the contact surface area 64" of sidewall 66" with a greater locking capability by allowing the screw head 24' to travel deeper into hole 54", as will be discussed in greater detail below.

For example, in the exemplary configuration shown in FIG. 23, the varying pitch of the triple lead threads 70", 90" provides for increasing a length of the density 84" or contact surface area 64" of sidewall 66" in a direction from the upper end 124 to the lower end 134 of hole 54". In particular, densities 84E, 84F and 84G can be narrower and/or shorter at a first level 178 than respective densities 84H, 84I and 84J and a second, lower level 182 in hole 54". In addition, such a configuration of increasing density of contact surface area 64" can aid in increasing the contact area for a non-locking (i.e., non-threaded) screw 14' in an area relative to a lower or base portion of the head 24', which can bear a significant portion of the force applied to head 24' in a compression arrangement.

Figure 24:
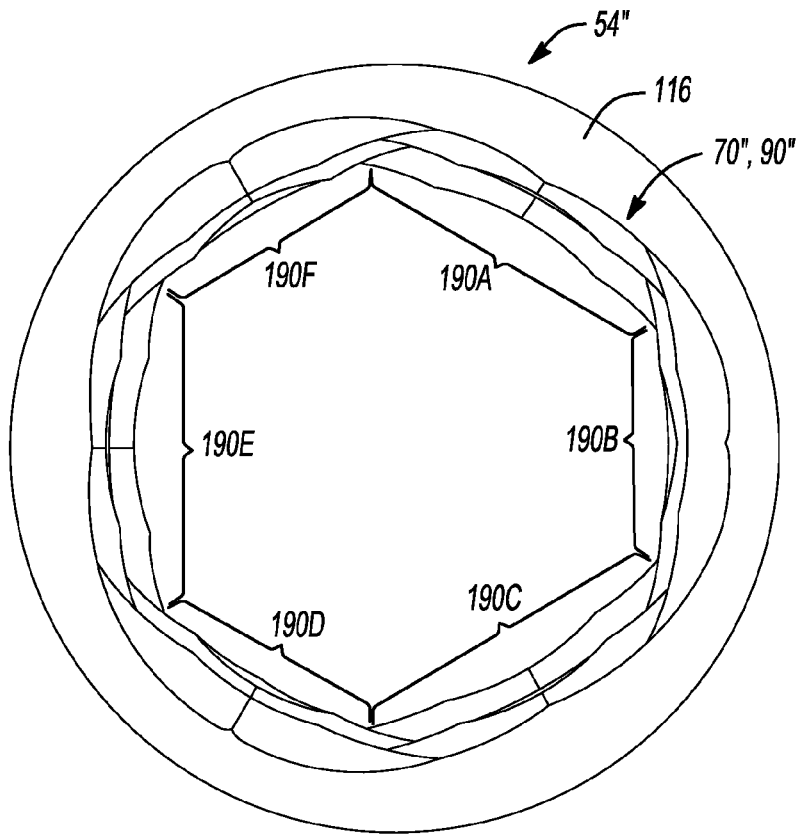
FIG. 24 is a top view of a portion of the bone plate and the bone plate hole of FIG. 21 in accordance with the present teachings.
Figure 25:
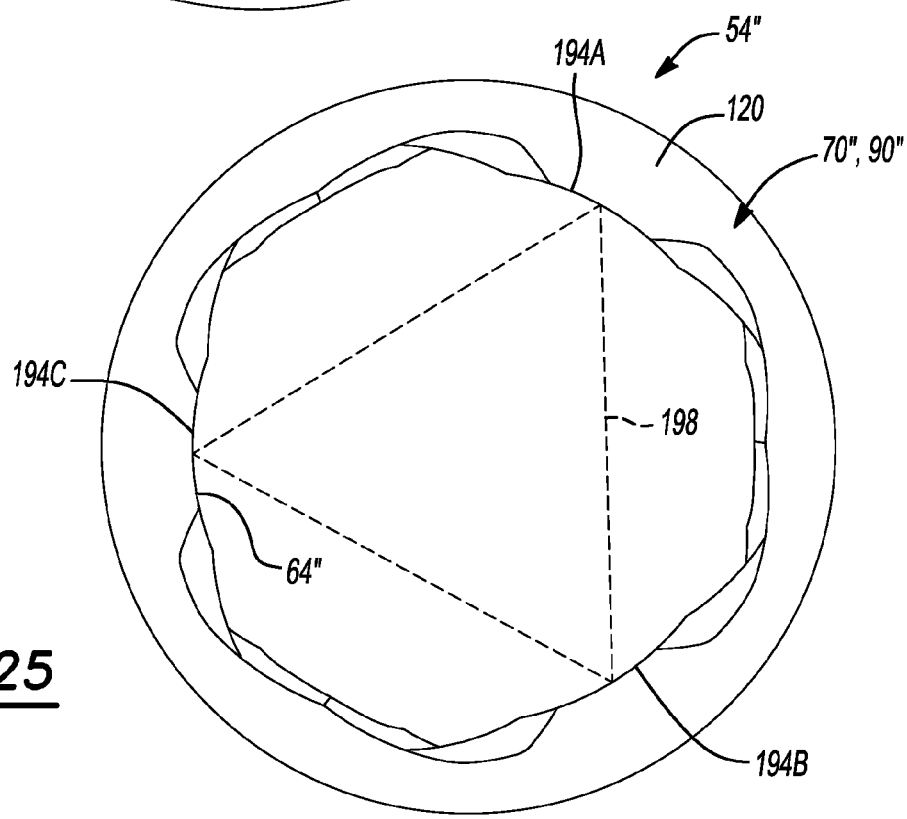
FIG. 25 is a bottom view of the bone plate and bone plate hole of FIG. 23 in accordance with the present teachings.

With additional reference to FIGS. 24 and 25, the triple lead right-hand and left-hand threads 70", 90" can provide for forming distinct areas of threads that are gradually discontinuous relative to each other. In the exemplary configuration of hole 54" shown in FIG. 24, the triple lead threads 70", 90" can form six distinct areas of threads 190A, 190B, 190C, 190D, 190E and 190F that are gradually discontinuous relative to each other. The thread areas 190A-190F can provide for varying contact with screw head 24' as head 24' is driven into hole 54" in various polyaxial orientations. This configuration of thread areas can also serve to reduce the amount of torque required to drive screw head 14' into hole 54". Furthermore, inclusion of the flats 154 on screw head 24' in connection with the thread areas 190A-190F can provide for further reducing the torque required to drive screw 14' into hole 54" as well as facilitate deeper engagement of head 14' in hole 54".

The triple lead threads 70", 90" formed in the manner discussed above can also provide for supporting areas 194 at the lower end 134 of hole 54", as can be seen in the bottom view of FIG. 25. In the exemplary configuration illustrated, the triple lead threads can form three supporting areas 194A, 194B and 194C. Supporting areas 194A-194C can be non-threaded areas of the contact surface area 64" and can provide for supporting a non-locking or compression screw in hole 54". In one exemplary configuration, the three supporting areas 194A-194C can be equally spaced apart from each other such that a substantially equidistant triangular configuration 198 can be formed relative to the three areas, as shown in phantom in FIG. 25.

The aforementioned screws and plates may, in exemplary forms thereof, be manufactured from any suitable biocompatible material, including titanium or stainless steel. However, it should be understood and appreciated herein that any suitable material may be utilized to fabricate the aforementioned components, including, without limitation, plastics, ceramics, metals, and alloys of the foregoing.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. An apparatus, comprising:
a plate member having a top surface and a bottom surface, the plate member defining a hole extending between the top and bottom surfaces, the hole having a spherically shaped sidewall;
a right-hand helical thread formed in the sidewall of the hole; and
a left-hand helical cut formed in the sidewall of the hole and intersecting the right-hand helical thread;
wherein the left-hand helical cut is configured to reduce a portion of a contact surface area of the right-hand helical thread and the sidewall.

2. The apparatus of claim 1, wherein the plate member hole defines a longitudinal axis, the right-hand helical thread and the left-hand helical cut formed in the sidewall concentrically about the longitudinal axis.

3. The apparatus of claim 1, wherein the left-hand helical cut comprises a left-hand helical thread.

4. The apparatus of claim 3, wherein the left-hand helical thread and the right-hand helical thread are each continuous.

5. The apparatus of claim 1, wherein the right-hand helical thread comprises a double lead right-hand helical thread, and wherein the left-hand helical cut comprises a left-hand helical thread.

6. The apparatus of claim 5, wherein the left-hand helical thread comprises a second pitch greater than a first pitch of the double lead right-hand helical thread.

7. The apparatus of claim 5, wherein the left-hand helical thread comprises a greater number of leads than the double lead right-hand helical thread.

8. The apparatus of claim 5, wherein the double lead right-hand helical thread comprises a first pitch, and wherein the left-hand helical thread comprises a double lead left-hand helical thread having a second pitch equal to two times the first pitch.

9. The apparatus of claim 5, wherein the double lead right-hand helical thread comprises a first pitch, and wherein the left-hand helical thread comprises a triple lead left-hand helical thread having a second pitch equal to two times the first pitch.

10. The apparatus of claim 5, wherein the double lead right-hand helical thread comprises a first pitch, and wherein the left-hand helical thread comprises a double lead left-hand helical thread having a second pitch equal to the first pitch.

11. The apparatus of claim 5, further comprising a fastener having a spherically shaped head and a shank extending therefrom, the spherically shaped head including a right-hand helical thread formed on an outer surface thereof and sized and shaped to be received in the plate member hole in a locking manner.

12. The apparatus of claim 11, wherein the right-hand helical thread of the spherically shaped head comprises a double lead right-hand helical thread configured to threadably engage the double lead right-hand helical thread of the plate member hole in a locking manner such that a longitudinal axis of the fastener is aligned with a longitudinal axis of the plate member hole.

13. The apparatus of claim 11, wherein the right-hand helical thread of the spherically shaped head comprises a double lead right-hand helical thread, and wherein the fastener is configured to be received in the plate member hole such that a longitudinal axis of the fastener is angled relative to a longitudinal axis of the plate member hole, the left-hand helical thread facilitating the double lead right-hand helical thread of the fastener cutting into the double lead right-hand helical thread and sidewall of the plate member hole by reducing an amount of contact surface area of the double lead right-hand helical thread and sidewall of the plate member hole.

14. The apparatus of claim 5, further comprising a fastener having a head and a shank extending therefrom, the head including a right-hand helical thread formed on an outer surface thereof and sized to be received in the plate member hole in a locking manner.

15. The apparatus of claim 14, wherein the right-hand helical thread and the left-hand helical thread formed in the sidewall include a triple lead right-hand helical thread and left-hand helical thread.

16. The apparatus of claim 15, wherein a pitch of the triple lead right-hand and left-hand helical threads includes a variable pitch that increases in a direction from the top surface to the bottom surface of the plate member.

17. A plating system for bone, comprising:
a plate member having a top surface and a bottom surface, the plate member defining a hole extending therebetween, the hole having a substantially spherical sidewall with a right-hand helical thread formed in the sidewall and a left-hand helical thread formed in the sidewall and intersecting the right-hand helical thread; and
a fastener having a head and a threaded shank extending therefrom, the head including a right-hand helical thread formed on an outer surface thereof;
wherein the fastener is configured to be received in the plate member hole in a first configuration whereby a longitudinal axis of the fastener is aligned with a longitudinal axis of the plate member hole, or in a second configuration whereby the longitudinal axis of the fastener is angled relative to the longitudinal axis of the plate member hole;
wherein the left-hand helical thread is configured to reduce a portion of a contact surface area of the plate member hole threads and sidewall to facilitate receiving the fastener head in the plate member hole in the second configuration in a locking manner.

18. The plating system of claim 17, wherein the fastener is configured to be received in the plate member hole in the second configuration whereby the right-hand fastener helical thread cuts into the right-hand helical thread and sidewall of the plate member hole, the left-hand helical thread reducing the portion of the contact surface area of the plate member hole right-hand helical thread and sidewall to facilitate the right-hand fastener helical thread cutting into the right-hand helical thread and sidewall of the plate member hole.

19. The system of claim 17, wherein the right-hand helical thread of the fastener is a continuous double lead right-hand helical thread; and
wherein the plate member hole right-hand helical thread and left-hand helical thread are each continuous.

20. The system of claim 17, wherein the right-hand helical thread of the plate member hole and the left-hand helical thread are formed in the sidewall concentrically about the longitudinal axis of the plate member hole such that the left-hand helical thread intersects the right-hand helical thread of the plate member hole.

21. The apparatus of claim 17, wherein the right-hand helical thread of the plate member hole comprises a double lead right-hand helical thread.

22. The system of claim 21, wherein the double lead right-hand helical thread of the plate member hole comprises a first pitch, and wherein the left-hand helical thread comprises a double lead left-hand helical thread having a second pitch equal to two times the first pitch.

23. The system of claim 21, wherein the double lead right-hand helical thread of the plate member hole comprises a first pitch, and wherein the left-hand helical thread comprises a triple lead left-hand helical thread having a second pitch equal to two times the first pitch.

24. The system of claim 21, wherein the double lead right-hand helical thread of the plate member hole comprises a first pitch, and wherein the left-hand helical thread comprises a double lead left-hand helical thread having a second pitch equal to the first pitch.

25. The system of claim 17, wherein the right-hand thread of the fastener includes a double-lead right hand helical thread, and wherein the right-hand and left-hand helical threads of the plate member hole include triple lead helical threads.

26. The apparatus of claim 25, wherein a pitch of the triple lead right-hand and left-hand threads includes a variable pitch that increases in a direction from the top surface to the bottom surface of the plate member.

27. The apparatus of claim 26, wherein the pitch of the triple lead right-hand and left-hand helical threads is greater than a pitch of the double lead right-hand helical thread of the fastener.

28. A plating system for bone, comprising:
a plate member having a top surface and a bottom surface, the plate member defining a hole extending between the top and bottom surfaces, at least a portion of the hole having a tapered sidewall;
a right-hand helical thread formed in the tapered sidewall of the hole; and
a left-hand helical thread formed in the tapered sidewall of the hole and intersecting the right-hand helical thread;
wherein the left-hand helical thread is configured to reduce a portion of a contact surface area of the right-hand helical thread and the tapered sidewall.

29. The plating system of claim 28, wherein the right-hand helical thread comprises a triple lead right-hand helical thread, and wherein the left-hand helical thread comprises a triple lead left-hand helical thread.

30. The plating system of claim 29, further comprising a fastener having a substantially spherically shaped head and a shank extending therefrom, the head including a double lead right-hand helical thread formed on an outer surface thereof and sized and shaped to be received in the tapered sidewall of the plate member hole in a locking manner.

31. The plating system of claim 30, wherein the fastener is configured to be received in the plate member hole such that a longitudinal axis of the fastener is angled relative to a longitudinal axis of the plate member hole, the triple lead left-hand helical thread facilitating the double lead right-hand helical thread of the fastener cutting into the threads and the tapered sidewall of the plate member hole by reducing an amount of contact surface area of the threads and tapered sidewall of the plate member hole.

32. A variable angle locking system, comprising:
a plate member having a threaded hole, the threaded hole including a sidewall having a right-hand thread and a left-hand thread formed therein; and
a fastener having a threaded head portion and an elongated shaft portion extending from the head portion, the threaded head portion being configured to lockably mate with the threaded hole of the plate member at more than one angle relative to a horizontal plane defined by the plate member;
wherein the right-hand thread and the left-hand thread of the plate member hole are configured to reduce a portion of a density of the sidewall.

33. The variable angle locking system of claim 32, wherein the right-hand thread has a first helix angle and the left-hand thread has a second helix angle, the first and second helix angles being the same.

34. The variable angle locking system of claim 32, wherein the plate member has an underside at least partially defined by an undercut, the undercut being configured to accommodate the elongated shaft portion of the fastener as the head portion of the fastener is lockably mated with the threaded hole of the plate member.

35. The variable angle locking system of claim 32, wherein the right-hand and left-hand threads are each triple lead helical threads.

36. The variable angle locking system of claim 35, wherein the threaded head portion of the fastener includes a double lead right-hand helical thread.

37. The variable angle locking system of claim 36, wherein the triple lead right-hand and left-hand threads each include a variable pitch.

38. The variable angle locking system of claim 37, wherein the variable pitch is the same for the triple lead right-hand and left-hand threads and increases from a top of the hole adjacent an upper surface of the plate member to a bottom of the hole adjacent an opposite lower surface of the plate member.

39. The variable angle locking system of claim 32, wherein the plate member is a bone plate.

40. The variable angle locking system of claim 32, wherein the head portion of the fastener includes a non-linearly tapered outer profile.

41. The variable angle locking system of claim 40, wherein the fastener has rounded edges between the non-linearly tapered outer profile and a back surface of the head portion.

42. The variable angle locking system of claim 32, wherein the head portion of the fastener includes one or more flats adapted to reduce fastener application torque and to allow the head portion of the fastener to engage deeper into the plate member as the head portion of the fastener is lockably mated with the threaded hole of the plate member.

43. The variable angle locking system of claim 32, wherein the fastener includes one or more tapping features near the elongated shaft portion of the fastener to ensure that the fastener and the plate member are fully engaged as the head portion of the fastener is lockably mated with the threaded hole of the plate member.

44. A variable angle locking system comprising:
a bone plate having an upper surface, a lower surface and a threaded hole extending therebetween, the threaded hole including a substantially spherical sidewall having a right-hand thread and a left-hand thread formed in the sidewall, wherein the right-handed and left-handed threads are each triple lead threads; and
a bone fastener having a threaded head portion and an elongated shaft portion extending from the head portion, the threaded head portion having a non-linearly tapered outer profile and a double lead thread formed on an outer surface thereof;
wherein the threaded head portion of the bone fastener is configured to lockably mate with the threaded hole of the bone plate at more than one angle relative to a horizontal plane defined by the bone plate;
wherein the right-hand and left-hand threads of the threaded hole are configured to reduce a portion of a density of the sidewall to facilitate receiving the threaded head portion of the bone fastener in a locking manner in various angles relative to the horizontal plane.

45. The variable angle locking system of claim 44, wherein the double lead thread of the bone fastener is a double lead right-hand helical thread.

46. The variable angle locking system of claim 45, wherein the double lead right-hand thread has a first pitch and the triple lead right-hand and left-hand threads have a second pitch greater than the first pitch.

47. The variable angle locking system of claim 46, wherein the second pitch is a variable pitch.

48. The variable angle locking system of claim 47, wherein the variable pitch includes a pitch that increases from a top of the hole adjacent an upper surface of the bone plate to a bottom of the hole adjacent an opposite lower surface of the bone plate.

49. The variable angle locking system of claim 44, wherein the bone plate has an underside at least partially defined by an undercut, the undercut being configured to accommodate the elongated shaft portion of the bone fastener as the head portion of the bone fastener is lockably mated with the threaded hole of the bone plate.

50. The variable angle locking system of claim 44, wherein the head portion of the bone fastener includes one or more flats adapted to reduce fastener application torque and to allow the head portion of the bone fastener to engage deeper into the bone plate as the head portion of the fastener is lockably mated with the threaded hole of the bone plate.

51. A variable angle locking system, comprising:
a bone plate having an upper surface and a lower surface and defining a hole extending therebetween, the hole having a substantially spherical sidewall with a triple lead left-hand helical thread and a triple lead right-hand helical thread formed in the sidewall, each of the triple lead right-hand and left-hand threads having a variable pitch that increases in a direction from the upper surface to the lower surface; and
a bone fastener having a threaded head portion and an elongated shaft portion extending from the head portion, the threaded head portion having:
a double lead right-hand helical thread formed on an outer surface thereof;
a non-linearly tapered outer profile; and
one or more flats forming a portion of the outer surface and adapted to reduce fastener application torque and to allow the head portion of the bone fastener to engage deeper into the bone plate as the head portion of the fastener is lockably mated with the threaded hole of the bone plate;
wherein the fastener is configured to be received in the bone plate hole in a locking manner in an orientation whereby a longitudinal axis of the fastener is aligned with a longitudinal axis of the bone plate hole and in various orientations whereby the longitudinal axis of the fastener is angled relative to the longitudinal axis of the bone plate hole;
wherein the left-hand and right-hand triple lead helical threads are configured to reduce a portion of a contact surface area of the bone plate threads and the sidewall to facilitate receiving the fastener in the bone plate hole in various polyaxial orientations in the locking manner.

52. The variable angle locking system of claim 51, wherein the bone fastener has rounded edges between the non-linearly tapered outer profile and a back surface of the head portion.

53. The variable angle locking system of claim 51, wherein the triple lead right-hand and left-hand threads formed in the sidewall of the bone plate hole form six discrete gradually discontinuous areas of threads around a circumference of the hole.

54. The variable angle locking system of claim 51, further comprising a lead-in chamfer extending between the upper surface of the bone plate and an upper end of the bone plate hole, and an undercut extending between the lower surface of the bone plate and a lower end of the bone plate hole.

* * * * *